United States Patent [19]

Rosback et al.

[11] 3,969,223

[45] July 13, 1976

[54] OLEFIN SEPARATION PROCESS

[75] Inventors: Donald H. Rosback, Elmhurst; Richard W. Neuzil, Downers Grove, both of Ill.

[73] Assignee: Universal Oil Products Company, Des Plaines, Ill.

[22] Filed: Dec. 11, 1974

[21] Appl. No.: 531,656

Related U.S. Application Data

[60] Continuation-in-part of Ser. No. 423,599, Dec. 10, 1973, abandoned, which is a division of Ser. No. 317,861, Dec. 22, 1972, Pat. No. 3,929,669.

[52] U.S. Cl. .................... 208/310 Z; 260/677 AD
[51] Int. Cl.$^2$ ........................................ C10G 25/04
[58] Field of Search ............. 208/310; 260/677 AD, 260/676 MS

[56] References Cited
UNITED STATES PATENTS

| | | | |
|---|---|---|---|
| 3,265,750 | 8/1966 | Peck et al. | 260/677 AD |
| 3,326,797 | 6/1967 | Young | 208/111 |
| 3,706,813 | 12/1972 | Neuzil | 260/676 MS |
| 3,717,572 | 2/1973 | Gramont et al. | 208/310 |

Primary Examiner—Herbert Levine
Attorney, Agent, or Firm—James R. Hoatson, Jr.; Thomas K. McBride; William H. Page, II

[57] ABSTRACT

An improved process for the separation of olefins from a hydrocarbon feed mixture comprising olefins and saturates which process uses a zeolite adsorbent to selectively adsorb the olefins. The improvement comprises employing a zeolite adsorbent produced by the steps of: contacting a precursor mass containing type X structured zeolite and amorphous material as a binder with an aqueous caustic solution to effect the addition of alkali metal cations to the crystalline structure; washing the mass with water to remove therefrom excess caustic solution; and, at least partially dehydrating said mass at dehydrating conditions thereby producing an adsorbent which has both increased capacity for olefins and decreased catalytic activity.

6 Claims, No Drawings

OLEFIN SEPARATION PROCESS

CROSS-REFERENCE TO RELATED APPLICATIONS

This application is a continuation-in-part application of our copending application Ser. No. 423,599 filed on Dec. 10, 1973, now abandoned which is a division of our copending application Ser. No. 317,861 filed on Dec. 22, 1972 now Pat. No. 3,929,669.

BACKGROUND OF THE INVENTION

1. Field of the Invention

The field of art to which this invention pertains is hydrocarbon separation. More specifically this invention relates to a process for separating olefins from a hydrocarbon feed mixture containing olefins and saturates which process employs a zeolitic adsorbent.

2. Description of the Prior Art

The treating of crystalline aluminosilicates with a caustic solution to modify certain of its properties has been recognized in the prior art. U.S. Pat. No. 3,326,797 for example, discloses a process for aqueous caustic treating of high silica zeolites having silica over alumina ratios between about 6 and 12, at treating conditions, for the sole purpose of removing a certain percentage of structural silica from the zeolite. The caustic treating, at conditions to preferably retain a final $SiO_2/Al_2O_3$ ratio greater than about 5.5, is found to increase the adsorptive capacity of the zeolite and to increase its catalytic activity. The caustic treating process of that reference patent is concerned only with etching or leaching of silica from the zeolite structure to achieve these characteristics and neither discloses nor suggests the addition of alkali metal cations to the zeolite structure during the treating process for any reaction whatever.

Other closely related prior arts are U.S. Pat. Nos. 3,265,750 by D. W. Peck et al and 3,717,572 by A. M. deGramont. The first patent relates to a process for the separation of olefins from paraffins and discloses that the adsorbent employed could be treated by various methods, such as treatment with an amine, to inhibit polymerization. The patent makes no reference to producing an adsorbent having an increased capacity for olefins. More specifically, that reference neither teaches nor suggests our treatment step of a precursor mass comprising a type X zeolite and an amorphous binder to increase the sodium content of the zeolite and to remove a small quantity of silica and alumina thereby producing an adsorbent having both decreased catalytic activity and increased capacity for olefins.

U.S. Pat. No. 3,717,572 discloses a method of neutralizing the acidity of molecular sieves, used to separate olefin-containing mixtures, thereby reducing isomerization and polymerization activity of the molecular sieves. The neutralization is effected by immersing the seive in a solution of an inorganic base. The solvent may be water or an organic solvent but an organic solvent is preferred, and in particular methanol, since in such case a complete neutralization of the sieve is obtained with a smaller consumption of base while maintaining a "practically unchanged adsorptive capacity of the sieve." The use of water as a solvent in the neutralization method of that reference has the disadvantage of lowering the adsorptive capacity of the sieve.

We have discovered that an adsorbent having both increased capacity for olefins and decreased catalytic activity for polymerization and isomerization can be prepared by the steps of: contacting a precursor mass comprising a type X zeolite and an amorphous binder haing a $Na_2O/Al_2O_3$ ratio of less than about 0.7 with an aqueous sodium hydroxide solution at ion-exchange conditions to increase the sodium cation content to a $Na_2O/Al_2O_3$ ratio of greater than about 0.7 and to remove not more than about 15 wt. % of $SiO_2$ and $Al_2O_3$ from the precursor mass; washing the mass with water to remove excess sodium hydroxide solution; and, at least partially dehydrating the mass at dehydrating conditions. We have found that catalytic activity of the finished adsorbent decreases in proportions to the amount of sodium cations added to the zeolite by the caustic treatment. Specifically, we have found that a sodium content, expressed as the ratio $Na_2O/Al_2O_3$, above about 0.7 is required to produce an adsorbent having the desired properties. The sodium cation added by the ion-exchange apparently replaces acid sites within the zeolite that catalyze isomerization and polymerization reaction. The removal of a small amount of silica and alumina from the precursor mass results in improved capacity of the adsorbent for olefins.

Employing the adsorbent so produced in a olefin separation process results in an improved olefin separation process because less adsorbent is required due to the adsorbent's increased capacity and because the adsorbent has a larger effective on-stream life due to its reduced cataytic activity.

SUMMARY OF THE INVENTION

The invention can be summarized as encompassing both a method for the manufacture of an adsorbent having both increased capacity for olefins and decreased catalytic activity and an improved adsorptive process for the separation of olefins from a hydrocarbon feed mixture comprising olefins and saturates. The adsorbent manufacturing method broadly comprises the steps of: contacting a precursor mass comprising type X zeolite with an aqueous caustic solution to effect the addition of alkali-metal cation to the zeolite structure, washing the mass of aluminosilicate with water to remove excess casutic solution and, at least partially dehydrating the washed adsorbent. The improved olefins separation process comprises the steps of: contacting a hydrocarbon feed mixture which comprises olefins and saturates with a bed of zeolite adsorbent at adsorption conditions to effect the selective retention of olefins by the adsorbent; withdrawing from the bed of adsorbent a raffinate stream comprising less selectively retained hydrocarbons; contacting the adsorbent bed with a desorbent material at desorption conditions to effect desorption of the olefins from the adsorbent; and, withdrawing a stream containing olefins and desorbent from the bed of adsorbent the improvement which comprises employing the adsorbent prepared by the method of this invention.

DESCRIPTION OF THE INVENTION

Since the anticipated use for the adsorbent prepared by the method described herein is in various processes for the separation of olefinic hydrocarbons from a feed mixture containing olefinic and saturated hydrocarbons, the particular usefulness of this adsorbent, general insight into its desirable characteristics, and the improvements accruing to the processes may be better understood by reference to those processes.

To separate olefins from a feed mixture comprising olefins and saturates the feed mixture is contacted with one or more beds of the adsorbent and the olefins are more selectively adsorbed and retained by the adsorbent while the less selectively adsorbed saturates are removed from the interstitial void spaces between the particles of adsorbent and the surface of the adsorbent. The adsorbent containing the more selectively adsorbed olefins is referred as a "rich" adsorbent--rich in the more selectively adsorbed olefins. The adsorbent is then contacted with a desorbent material which is capable of displacing the adsorbed olefinic hydrocarbons from the adsorbent.

The more selectively adsorbed feed components are commonly referred to as the extract components of the feed mixture, while the less selectively adsorbed components are referred to as the raffinate components. Fluid streams leavng the adsorbent comprising an extract component and comprising a raffinate component are referred to, respectively, as the extract stream and the raffinate stream. Thus, the raffinate streamm will contain as raffinate components essentially all of the feed saturates and the extract stream will contain essentially all of the feed olefins as the extract components.

Although it is possible by the process of this invention to produce high purity (98% or greater), olefins at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of extract components and raffinate components both appearing in the particular stream. For example, the ratio of concentration of the more selectively adsorbed feed olefins to the concentration of less selectively adsorbed feed saturates will be highest in the extract stream, next highest in the feed mixture, and lowest in the raffinate stream. Likewise, the ratio of the less selectively adsorbed feed saturates to the more selectively adsorbed feed olefins will be highest in the raffinate stream, next highest in the feed mixture, and the lowest in the extract stream.

The adsorbent can be contained in one or more chambers where through programmed flow into and out of the chambers separation of the olefin is effected. The adsorbent may be contacted with a desorbent material which is capable of displacing the adsorbed olefins from the adsorbent. Alternatively, the olefins could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described). In the simplest embodiment of the invention the adsorbent is employed in the form of a single static bed in which case the process in only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the adsorbent. Any of the conventional apparatus employed in static bed fluid-solid contacting may be used.

Moving-bed or simulated moving-bed systems, however, have a much greater separation efficiency than fixed adsorbent bed systems and are therefore preferred.

Specifically, the more preferred processing flow schemes which can be utilized to effect the process of this invention are those known in the art as simulated moving-bed countercurrent systems. One such system includes the flow scheme described in U.S. Pat. No. 2,985,589 issued to D. B. Broughton. This patent generally described the processing sequence involved in a particular simulated moving-bed countercurrent solidfluid contacting process. In fact, the processing sequence generally described in that patent is the preferred mode of operating the separation process disclosed herein. More specifically that processing sequence is employed in the olefin separation process described in U.S. Pat. No. 3,510,423 issued to R. W. Neuzil et al. In a preferred embodiment our process is an improved process of that described in the Neuzil et al patent.

With these references in mind therefore, one embodiment of our invention is an improved process for separating olefins from a feed mixture comprising olefins and saturates which process comprises the steps of: contacting the feed mixture at adsorption conditions with a bed of zeolitic adsorbent to effect the selective adsorption of said olefins by said adsorbent; withdrawing from the bed of adsorbent a raffinate stream comprising the less selectively adsorbed saturates; contacting the adsorbent bed at desorption conditions with a desorbent material to effect the desorption of the olefins from the adsorbent; and, withdrawing from the bed of adsorbent a stream comprising desorbent material and olefins the improvement which comprises employing a zeolite adsorbent prepared by the steps of: (a) contacting a precursor mass comprising a type X structured zeolite and an amorphous binder selected from the group consisting of silica, alumina, and silica and alumina and having a $Na_2O/Al_2O_3$ ratio of less than about 0.7 with an aqueous sodium hydroxide solution at ion-exchange conditions to increase the sodium cation content to a $Na_2O/Al_2O_3$ ratio of greater than about 0.7 and to remove not more than about 15 wt. % of $SiO_2$ and $Al_2O_3$ from the precursor mass; (b) washing the mass with water maintained at a pH within the range of 7 to 10 to remove therefrom excess sodium hydroxide; and, (c) at least partially dehydrating the mass at dehydrating conditions.

Preferred operating conditions for both adsorption and desorption of this particular embodiment of our invention includes a temperature within the range of from about 25° C. up to about 150° C. and a pressure within the range of from about atmospheric to about 500 psig. Furthermore, both adsorption and desorption are preferably affected at conditions selected to maintain liquid phase throughout the process operation.

Adsorption and desorption could, of course, be conducted both in the vapor phase or liquid phase or one operation may be conducted in the vapor phase and the other in the liquid phase. Operating pressures and temperatures for adsorption and desorption might be the same or different.

The desorbent materials which can be used in the various processing schemes employing this adsorbent will vary depending on the type of operation employed. The term "desorbent material" as used herein means any fluid substance capable of removing a selectively adsorbed feed component from the adsorbent. In the swing-bed system in which the selectively adsorbed feed component is removed from the adsorbent by a purge stream, gaseous hydrocarbons such as methane, ethane, etc., or other types of gases such as nitrogen or hydrogen may be used at elevated temperatures or reduced pressure or both to effectively purge the adsorbed feed component from the adsorbent.

However, in processes which are generally operated at substantially constant pressures and temperatures to insure liquid phase, the desorbent material relied upon must be judiciously selected in order that it may displace the adsorbed feed component from the adsorbent with reasonable mass flow rates and also without unduly preventing the extract component from displacing the desorbent in a following adsorption cycle.

Desorbent materials which can be used in the process of this invention should additionally be substances which are easily separable from the feed mixture that is passed into the process. In desorbing the preferentially adsorbed component of the feed, both desorbent material and the extract component are removed from the adsorbent in admixture. Without a method of separation of these two materials, the purity of the extract component of the feed stock would not be very high since it would be diluted with desorbent. It is contemplated that any desorbent material used in this process will have a substantially different average boiling point than that of the feed mixture. More specifically, "substantially different" shall mean that the difference between the average boiling points shall be at least about 20°F. The boiling range of the desorbent material could be higher or lower than that of the feed mixture. The use of a desorbent material having a substantially different average boiling point than that of the feed allows separation of desorbent material from feed components in the extract and raffinate streams by simple fractionation or other methods thereby permitting reuse of desorbent material in the process.

In the preferred isothermal, isobaric, liquid-phase operation of the process of this invention, desorbent materials comprising olefins are particularly effective and preferred. Specifically, desorbent materials comprising straight-chain and branched-chain olefins having average boiling points substantially different from the feed mixture and having selectivities (hereinafter discussed in more detail) with respect to the feed olefins of about 1.0 are particularly preferred.

Mixtures of olefins with paraffins have, additionally, been found to be effective desorbent materials. The paraffins can include straight- or branched-chain paraffins or cycloparaffins having a boiling point substantially different from the feed to allow separation from feed components. Typical concentration of olefins used in admixture with a paraffin can be from a few volume percent up to near 100 vol. % of the total desorbent material and preferably will be within the range of from about 25 vol. % to about 100 vol. % with an even more preferred range being from about 50 vol. % to about 100 vol. % of the total desorbent material.

The adsorbent produced by the method of this invention may of course be used in other selective adsorption processes for separating olefins. These might include, for instance, swing-bed processes in which both adsorption and desorption are conducted in the vapor phase or in which one operation is conducted in the vapor phase and the other in the liquid phase. Operating pressures and temperatures for adsorption and desorption might be the same or different.

Charge stocks which may be used in the above or other selective adsorption processes may contain olefins from about $C_4$ to about $C_{20}$ carbon range. If the feed mixture contains more than one olefins in this carbon number range, it is preferred that they be homologs of each other. Of these olefins, the $C_{10}$–$C_{15}$ range is particularly preferred. The $C_{10}$–$C_{15}$ normal mono-olefins are generally produced by catalytically dehydrogenating a $C_{10}$–$C_{15}$ normal paraffin stream. The effluent stream from a dehydrogenation process generally contains about 5 to 25% olefins and may require further processing in order to concentrate the normal olefinic hydrocarbons.

A typical example of the composition of the effluent stream from a dehydrogenation process is shown in Table I:

TABLE I

| DEHYDROGENATION REACTOR EFFLUENT ANALYSIS BY GAS-LIQUID CHROMATOGRAPHY | | |
|---|---|---|
| | | Wt. % |
| n-$C_{10}$ paraffin | | 0.1 |
| n-$C_{11}$ paraffin | | 24.9 |
| n-$C_{11}$ olefin | | 1.8 |
| n-$C_{12}$ paraffin | | 27.8 |
| n-$C_{12}$ olefin | | 2.6 |
| n-$C_{13}$ paraffin | | 22.6 |
| n-$C_{13}$ olefin | | 2.7 |
| n-$C_{14}$ paraffin | | 12.1 |
| n-$C_{14}$ olefin | | 1.7 |
| n-$C_{15}$ paraffin | | 0.4 |
| Total non-normals | | 3.3 |
| | TOTAL | 100.0 |
| Total non-normals | | 3.3 |
| Total normal olefins | | 8.8 |
| Total normal paraffins | | 87.9 |
| | TOTAL | 100.0 |
| | | Vol.% |
| Total olefins | | 9.8 |
| Light ends | | 0.2 |
| Total paraffins | | 86.5 |
| Total non-normals | | 3.5 |
| | TOTAL | 100.0 |

The 3.5 volume percent non-normals in the above analysis are primarily aromatics. Another possible charge stock for the process would be a selected fraction from a gasoline produced by a fluid catalytic cracking unit. A typical analysis, from a 95°C. cut of such gasoline is as follows:

| | Vol% |
|---|---|
| Olefins | 25.4 |
| Paraffins and naphthenes | 72.3 |
| Aromatics | 2.3 |
| | 100.0 |

With the type of processes employing adsorbents to separate olefins now in mind, one can appreciate that certain characteristics of adsorbents are highly desirable, if not absolutely necessary, to the successful operation of the selective adsorptive process. Among such characteristics are: adsorptive capacity for some volume of desired olefins per volume of adsorbent; reduced or eliminated catalytic activity for undesired side reactions such as polymerization and isomerization; and selectivity of adsorption both for olefins and for the desired carbon number range of olefins.

Capacity of the adsorbent for adsorbing a specific volume of olefins is of course a necessity; without such capacity the adsorbent is useless for adsorptive separation. Furthermore the higher the adsorbent's capacity for the species to be adsorbed, the better is the adsorbent. Increased capacity of a particular adsorbent makes it possible to reduce the amount of adsorbent needed to separate the desired species contained in a particular rate of hydrocarbon feed mixture. A reduction in the amount of adsorbent required for a specific adsorptive separation directly reduces the cost of the separation process. It is important that the good initial capacity of the adsorbent be maintained during actual use in the separation process over some economically desirable life.

For this reason, and others, it is necessary that the adsorbent possess little or no catalytic activity which would produce products that might degrade adsorbent capacity or selectivity. It is additionally important that the highly reactive olefins are not reacted into side products which either degrade the product quality or reduce the overall yield of concentrated olefins. In instances where the feed streams include both normal and isomeric olefin hydrocarbons, the isomerization effects of the adsorbent are not a great impediment to the process economics where the prime consideration is the concentration of olefinic product streams. However, reduction of the polymerization activity of an adsorbent is very important. The polymerization, in addition to reducing the yields of olefinic hydrocarbons also, as mentioned above, tends to degrade the adsorbent. The polymerization effects are generally considered to be primarily physical impediments which can prevent the olefinic hydrocarbons from passing into the molecular sieve adsorbent by plugging up the surface of the adsorbent and the pores present in the structure of the adsorbent. This shortens the useful life of the adsorbent and makes necessary frequent regeneration treatments to restore the adsorptive properties of the adsorbent.

In instances where a particular isomer of a normal olefinic hydrocarbon is desired to be separated from a feed stream which contains primarily a single olefinic isomer, the isomerization activity of the adsorbent becomes an equal if not greater problem than the polymerization activity. Since both reactions seem to occur at the same time, the term "catalytic activity" as used herein shall mean both isomerization and polymerization activity. It is, therefore, extremely important that the catalytic activity be substantially reduced or preferably totally eliminated by proper methods of manufacture of a selected adsorbent.

While reducing the temperature of the operations of the adsorption process in which the catalytic activity is present will substantially reduce the catalytic activity because of the associated reduction in the rate of reaction, this procedure is adsorptive separation processes employing molecular sieves, in most cases, is not desirable because the reduction in temperature also reduces the kinetic energy of the materials passing into and out of the adsorbent. This substantially reduces the rate of exchange of feed olefins into and out of the adsorbent giving what is considered in the art as poor breakthrough fronts which result in product contamination with feed stock and relatively high requirements of adsorbent for a given throughput of olefin-containing feed stock.

The other important adsorbent characteristic is the ability of the adsorbent to separate components of the feed; or, in other words, the selectivity, (B), of the adsorbent for one component as compared to another component. Selectivity is expressed not only for the desired hydrocarbon type (olefins) as compared to undesired hydrocarbons but is also expressed between homologs of the desired hydrocarbon type. The selectivity, (B), as used throughout this specification is defined as the rate of the two components of the adsorbed phase over the ratio of the same two components in the unadsorbed phase at equilibrium conditions.

Selectivity is shown as Equation 1 below:

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions as defined here were determined when the feed passing over a bed of adsorbent did not change composition after contacting the bed of adsorbent. In other words, there was no net transfer of material occurring between the unadsorbed and adsorbed phases.

As can be seen where the selectivity of two components approaches 1.0 there is no preferential adsorption of one component by the adsorbent. As the (B) becomes less than or greater than 1.0 there is a preferential selectivity by the adsorbent of one component. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Desorbents ideally would have a selectivity equal to about 1 or slightly less than 1.

The adsorbent produced by the method of this invention has good selectivity for olefins, higher capacity for olefins, and little or no catalytic activity thereby making possible an improved process for the separation of olefins.

In order to test various adsorbents to measure the characteristics of adsorptive capacity, selectivity, and degree of catalytic activity, a dynamic testing apparatus was employed. The apparatus used consisted of an adsorbent chamber of approximately 40 cc. volume having inlet and outlet portions at opposite ends of the chamber. The chamber was contained within a temperature control means and, in addition, pressure control equipment was used to operate the chamber at a constant predetermined pressure. Attached to the outlet line of the chamber was chromatographic analysis equipment which was used to analyze the effluent stream leaving the sorbent chamber.

The actual operations used to determine the adsorbent capacity were as follows. A feed mixture containing at least one adsorbable component in a dilute component was passed through the adsorbent bed until the effluent stream leaving the adsorbent chamber, as measured by the chromatograph, was essentially the same composition as the feed stream passing into the inlet of the sorbent chamber. Generally the adsorbable component used in the feed mixture is decene-1. This indicates that the sieve has reached equilibrium, that is, the adsorbent was no longer adsorbing materials from the external phase and that there was no longer a net transfer of the material between the adsorbed phase and the external phase.

A desorbent mixture, containing an adsorbable component different from that of the feed, in a diluent component, was then passed into the adsorbent chamber at conditions to effect desorption of the previously adsorbed feed mixture component. Octene-1 is usually used as the adsorbable component in the desorbent mixture. The desorbent mixture was continuously passed into the adsorbent chamber until the effluent material, as monitored by the chromatographic equipment was substantially identical to the desorbent feed material, indicating that equilibrium conditions had been achieved. Knowing the flow rate to the chamber and the effluent composition as continuously monitored by the chromatograph, the total amount of the components adsorbed by the adsorbent from the desorbent mixture can be calculated.

In order to determine the adsorptive capacity of the sieve for components in the feed mixture, the inlet stream to the chamber was then switched from the desorbent mixture back to the feed mixture to allow feed components to displace the previously adsorbed components from the desorbent mixtures. Again using the chromatograph and knowing the flow rate and effluent composition, the volume of feed components adsorbed can be calculated.

Selectivity can then be calculated using the previously mentioned equation for selectivity and the capacities determined above.

In measuring the polymerization activity of the type X adsorbent, the same gas chromatographic equipment and testing apparatus was used. Two variations of the polymerization test can be used. In the first variation, the degree of catalytic activity may be measured by the loss of a known concentration of feed olefins as detected in the effluent stream by the chromatographic equipment. The measure of polymerization is then an indirect determination, being related to the difference between the inlet and outlet olefin concentrations. This catalytic activity is thought to be primarily due to polymerization reactions of the feed olefins with a small part of the feed olefins that are isomerized to other interal olefinic isomers. The relative activity scale used to express the catalytic activity of the adsorbent is determined by measuring the peak height of the chromatograph equivalent to the inlet concentration of olefin as indicative of a zero catalytic activity. Hence, if the peak height of the olefins present in the effluent is same as the peak height of a known concentration of olefins present in the feed, the relative adsorbent activity is zero. An effluent peak height equal to one half that of the feed would represent exactly 50% polymerization or isomerization of the feed olefin component. The adsorbent activity would therefore be 50%. Equation 2 below represents the formula used to determine catalytic activity of an adsorbent knowing the peak height of the olefins remaining in the effluent stream leaving the adsorbent chamber and the peak height of the olefins present in the feed.

EQUATION 2

$$\text{Adsorbent Activity} = 100 - 100 \frac{(Pe)}{(Pf)}$$

where Pe represents the peak height of the effluent olefins and Pf represents the peak height of the feed olefins.

The second variation of the catalytic activity test is to measure the polymer formed directly in the effluent stream with the chromatographic equipment. This method depends upon selecting a feed olefin, such as diisobutylene, that easily forms an identifiable polymer. The dimer peak height above the base line is then used as the measure of polymerization and catalytic activity is reported as dimer units. Both test variations can be used with the second method being the more sensitive in determining catalytic activity.

To translate this type of adsorbent capacity, selectivity, and activity data into actual olefin separation process performance requires actual testing of the adsorbent with various feed mixtures and desorbent materials in a countercurrent liquid-solid contacting device. The general operating principles of such a device has been previously described and are found in Broughton U.S. Pat. No. 2,985,589. A specific laboratory-size apparatus utilizing these principles is described in de Rosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are being withdrawn through two more. All remaining access lines are inactive and when the position of the distributing valve is advanced by one index, all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. de Rosset, R. W. Neuzil, D. J. Korous, and D. H. Rosback presented at the American Chemical Society, Los Angeles, Calif., Mar. 28 through Apr. 2, 1971.

The improvement in the olefin separation process that resulted from employing the adsorbent prepared as described herein was confirmed by continuous testing in the laboratory-sized apparatus described above.

The crystalline aluminosilicate contained in the starting material used in the method of this invention is generally referred to in the art as a type X structured zeolite and has the general empirical formula as shown in Equation 3 below:

EQUATION 3

$(0.9\pm0.2)M_{2/n}O:Al_2O_3:(2.5\pm0.5)SiO_2:yH_2O$ )SiO where M represents at least one cation having a valence of not more than 3, n represents the valence of M, and y is a value up to about 8 depending upon the identity of M and the degree of hydration of the crystal. The cation "M" may be one or more of a number of cations such as the hydrogen cation, the alkali metal cations, or the alkaline earth cations or other selected cations. The type X zeolite is specifically disclosed in U.S. Pat. No. 2,882,244 and in that reference patent the composition of a type X zeolite is shown along with the various methods of manufacturing it.

The starting material which is used in the process of this invention for 13X of an adsorbent particle is referred to in this presence 2.6. specification as a precursor material can be and comprises the type X crystalline aluminosilicate and a portion of amorphous material. The crystalline aluminosilicate material can be present in concentrations ranging from about 80 to about 98% of the weight of the precursor mass based on volatile free composition. Volatile free compositions are generally determined after the precursor mass has been calcined at 900° C. in order to drive off all volatile matter. The remaining material in the precursor mass generally comprises amorphous silica or alumina or both which is present in intimate mixture with the small particles of the zeolite material. This amorphous material may be an adjunct of the manufacturing process for the type X zeolite (for example, intentionally incomplete purification of the type X zeolite during its manufacture) or it may be added to relatively pure type X zeolite to aid in extrusion or pelleting of the zeolite.

A particularly preferred starting material is nominal 1/16 extrudate comprising 13X zeolite and a minor amount of amorphous material as binder. This zeolite is primarily in the sodium form; that is, the cation represented as M in equation 3 above is primarily sodium. By chemical analysis the $Na_2O/Al_2O_3$ ratio is less than about 0.7 and is typically about 0.6 or less which, it should be noted, is less than the 0.9±0.2 indicated in equation 3 above. Other cations present, primarily as impurities, typically include H+ and any of the Group IIA metal cations. It is believed that the presence of H+ is the primary cause of the catalytic activity possessed by this starting material. The silica to alumina ratio of this starting material by X-ray determination is about 2.5 and the same ratio by chemical analysis is about 2.6. Normally the starting material whether in the extrudate or pellet form is granulated to a particle size range of about 16–40 mesh (Standard U.S. Mesh) before the caustic treatment step is begun. This is approximately the desired particle size of the finished adsorbent.

The caustic treatment step is primarily an ion exchange step in which sodium cations replace non-sodium cation impurities in the zeolite-containing starting material thereby reducing or eliminating the catalytic activity of the zeolite. Although mild ion exchange conditions are employed, this step additionally removes a small amount of silica or silica and alumina thereby increasing the capacity of the material for olefins. Total silica and alumina removal from the precursor mass is from about 1 to about 15 % and is generally in the range of 5 to 15%. Further evidence of this is the increase in the percent zeolite, (as determined by X-ray analysis) and surface area and also the slight reduction in the $SiO_2/Al_2O_3$ ratio of the starting material. The silica or silica and alumina removed is thought to be primarily a portion of the amorphous binder whether silica or alumina or both, in the precursor mass, as evidenced by the closer agreement of the $SiO_2/Al_2O_3$ ratio of the finished adsorbent as determined by both chemical analysis and by X-ray.

We have found not only that this ion exchange step significantly reduces catalytic activity but specifically that the amount of activity reduction is proportional to the amount of sodium cation contained by the finished adsorbent. This relationship, with the amount of sodium expressed as the ratio $Na_2O/Al_2O_3$, indicated in Table 2 below. Catalytic activity for the 13X starting material and the various adsorbents was determined using the more sensitive of the activity tests previously described.

TABLE 2

Relationship Between $Na_2O/Al_2O_3$ and Catalytic Activity

| Adsorbent | $Na_2O/Al_2O_3$ | Catalytic Activity (Dimer Units) |
|---|---|---|
| 13X starting material | .61 | 55 |
| A | .78 | 4.5 |
| B | .81 | 3.75 |
| C | .83 | 2.35 |
| D | .85 | 2.05 |
| E | .88 | 1.10 |
| F | .91 | 0 |

As shown in the table, catalytic activity decreases with increasing sodium ion content from an unacceptable 55 dimer units of the starting material to about zero as the $Na_2O/Al_2O_3$ ratio approaches 1. For an acceptable adsorbent it is preferred that the $Na_2O/Al_2O_3$ ratio of the final product be greater than about 0.70.

Ion exchange conditions should be so regulated to achieve this desired degree of ion exchange. The degree of ion exchange achieved is a function of the three variables of caustic concentration, temperature at which the ion exchange is conducted, and the length of time the ion exchange is continued.

The ion exchange solutions employed herein are preferably composed essentially of alkali metal hydroxides, preferably sodium hydroxide, dissolved in water. Suitable concentrations to obtain the desired ion exchange can be from about 0.5 to 10 % by weight of the alkali metal hydroxide with the preferred concentration being from about 0.5 to 5 % by weight. By using solutions of these concentrations, the desired ion exchange can be obtained at temperatures from about 50° to 300° F. with temperatures from about 150° to 250° F. being preferred. Operating pressure is not critical and need only be sufficient to insure a liquid phase. Operating pressures can range from about atmospheric pressure to about 100 psig. The length of time required for the ion exchange will vary depending upon the solution concentration and temperature from about 0.5 to 5 hours. At the above preferred concentration and temperatures, a contact time which has been shown to be specifically preferred and which will produce the desired results is from about 2 to about 3 hours. The ion exchange step should be within the preferred concentration and time ranges noted above so that the zeolite structure will not be destroyed and so that the final product will have a $Na_2O/Al_2O_3$ ratio greater than about 0.7.

The next step in the method of manufacture of this invention is the washing step for the purpose of removing excess alkali metal hydroxide solution remaining within the ion-exchanged adsorbent mass. The washing medium is water which has a pH within the range of 7 to 10 and preferably within the range of 9 to 10. If necessary the water is adjusted to and maintained at the desired pH by adding alkali metal hydroxide. Since the primary purpose of the ion exchange was to remove hydrogen cation (and metal cation) contaminants, this pH range is necessary to avoid redepositing hydrogen cation on the adsorbent mass. Washing temperatures can include temperatures within the range of about 100° to about 200° F. with a temperature of 135° to 145° F. preferred. Although the washing step can be done in a batch manner with one aliquot of wash water at a time, the washing step is generally and preferably done on a continuous flow type basis with water passed through a bed of the adsorbent at a given liquid hourly space velocity and a temperature for a period of time in order that from about 1 to about 5 gallons of water per pound of starting material is used to wash the material. Preferred washing conditions include using liquid hourly space velocities from about 0.5 to about 5, with 1.5 being preferred, to pass from about 1 to about 3 gallons of wash water per pound of starting material over the ion exchanged adsorbent. A good indication of complete washing is made by measuring the pH of the effluent wash water and comparing it to the pH of the fresh feed wash water. When they are the same, washing can generally be considered as complete.

When the wash step is completed the wet adsorbent particles will usually contain from about 30 to about 50 wt. % volatile matter (water) as measured by loss on ignition to 900° C. The remaining step in the method of manufacture then is the drying step in which the volatile content of the washed adsorbent is reduced to less than about 10 wt. % with the preferred volatile content being about 5 to 7 wt. %. Drying conditions include the presence of air and can include temperatures from about 100° F. to about 1000° F. The time required to achieve the desired volatile content will vary depending upon the drying temperature and the exact volatile content of the water-washed adsorbent particles to be dried.

The following example is presented to demonstrate the method of this invention and the improved properties of an adsorbent prepared by the method of this invention. The example is not intended to unduly limit the scope and spirit of the appended claims.

EXAMPLE

An adsorbent, containing type X zeolite and having improved capacity for olefins and acceptably low catalytic activity, was produced using the following procedure.

Nominal 1/16-inch type 13X extrudate, obtained from Union Carbide Linde Division, was ground to produce 16–40 U.S. Standard mesh particle size material having physical and chemical properties as shown in Table No. 3 below. Olefin capacity and catalytic activity shown in the table were obtained using the testing apparatus and procedures previously described.

TABLE 3

| Properties of the Starting Material | |
|---|---|
| Chemical Properties | |
| Volatile Matter | |
| (loss on ignition at 900° C.), wt. % | 3.2 |
| $SiO_2$ (volatile free) wt. % | 50.7 |
| $Al_2O_3$ (volatile free) wt. % | 33.6 |
| $Na_2O$ (volatile free) wt. % | 12.4 |
| $Na_2O/Al_2O_3$ | .61 |
| $SiO_2/Al_2O_3$ | 2.56 |
| | |
| Physical Properties | |
| Apparent Bulk Density, gm/cc | 0.635 |
| Surface Area, m²/gm | 500 |
| Pore Volume, ml/gm | 0.30 |
| Pore Diameter, A | 24 |
| Area % faujasite (X-ray) | 93 |
| $SiO_2/Al_2O_3$ (X-ray) | 2.5 |
| Particle Size Distribution: | |
| Wt. % on 16 U.S. Screen | 0.3 |

TABLE 3-continued

| Properties of the Starting Material | |
|---|---|
| on 20 | 33.3 |
| on 30 | 37.9 |
| on 40 | 21.4 |
| on 56 | 6.1 |
| on 60 | 0.3 |
| through 60 U.S. Screen | 0.7 |
| | |
| Testing Data | |
| Olefin Capacity: | |
| $A_8$, cc of octene-1/40 cc adsorbent | 3.1 |
| $A_{10}$, cc of decene-1/40 cc adsorbent | 2.8 |
| Catalytic Activity, Dimer Units | 55 |

One hundred pounds of the granular starting material was loaded into an ion exchange tower against an upward flow of 1.6 wt. % NaOH solution at a rate such that the effluent temperature did not exceed 145° F. After all of the material was loaded, the material was ion exchanged by passing the 1.6 wt. % NaOH solution upflow through the ion exchange tower at a liquid hourly space velocity of 1.5 and a temperature of 200°F. until a total of 0.335 pounds of NaOH per pound of volatile-free starting material had been passed through the tower.

After the ion exchange the water wash step was begun. The ion exchanged material was water washed by passing treated water, having a pH of 10, upflow through the tower at 1.5 LHSV and 140° F. to a total of 1.3 gallons of water per pound of volatile free starting material.

The washed material was then dewatered, unloaded from the ion exchange tower, and dried in a forced air oven at 570° F. to a volatile content of 5.0 wt. %. An overall yield of 72% dried 16–40 U.S. mesh granular adsorbent was obtained by this procedure. Properties of the finished adsorbent are shown in Table No. 4 below:

TABLE 4

| Properties of the Finished Adsorbent | |
|---|---|
| Chemical Properties | |
| Volatile Matter | |
| (loss on ignition at 900° C.), wt. % | 5.0 |
| $SiO_2$ (volatile free) wt. % | 48.0 |
| $Al_2O_3$ (volatile free) wt. % | 32.1 |
| $Na_2O$ (volatile free) wt. % | 15.8 |
| $Na_2O/Al_2O_3$ | 0.81 |
| $SiO_2/Al_2O_3$ | 2.54 |
| | |
| Physical Properties | |
| Apparent Bulk Density, gm/cc | 0.671 |
| Suface Area, m²/gm | 516 |
| Pore Volume, ml/gm | 0.27 |
| Pore Diameter, A | 21 |
| Area % faujasite (X-ray) | 110 |
| $SiO_2/Al_2O_3$ (X-ray) | 2.5 |
| Particle Size Distribution: | |
| Wt. % on 16 U.S. Screen | 0.0 |
| on 20 | 22.7 |
| on 30 | 37.1 |
| on 40 | 29.0 |
| on 56 | 8.2 |
| on 60 | 0.1 |
| through 60 U.S. Screen | 2.9 |
| | |
| Testing Data | |
| Olefin Capacity: | |
| $A_8$, cc of octene-1/40 cc adsorbent | 3.78 |
| $A_{10}$, cc of decene-1/40 cc adsorbent | 3.35 |
| Catalytic Activity, Dimer Units | 3.9 |

Testing results shown in tables 3 and 4 show that the adsorbent olefin capacity has been increased from 3.1 to 3.78 cc of octene-1 per 40 cc of adsorbent or about 22and from 2.8 to 3.35 cc of decene-1 per 40 cc of adsorbent or about 20 %. As importantly, the catalytic activity has been substantially decreased from 55 dimer units to an acceptable activity of 3.5 dimer units. $Na_2O$ content of the adsorbent has been increased about 25% from 12.4 wt. % to 15.8 wt. % with less than about 15% reduction each in the $SiO_2$ and $Al_2O_3$ content.

We claim as our invention:

1. In a process for the separation of olefins from a hydrocarbon feed mixture comprising olefins from a hydrocarbon feed mixture comprising olefins and saturates, which process comprises the steps of:
   a. contacting said feed mixture with a bed of zeolite adsorbent at adsorption conditions to effect the selective adsorption of said olefins by said adsorbent;
   b. withdrawing from said bed of adsorbent a raffinate stream comprising less selectively adsorbed saturates;
   c. contacting the adsorbent bed with a desorbent material at desorption conditions to effect desorption of said olefins from said adsorbent; and,
   d. withdrawing a stream containing olefins and desorbent material from said bed of adsorbent; THE IMPROVEMENT WHICH COMPRISES employing a zeolite adsorbent prepared by the steps of:
   i. contacting a precursor mass comprising an X structured zeolite, and an amorphous binder selected from the group consisting of silica, alumina, and silica-alumina, and having a $Na_2O/Al_2O_3$ ratio of less than about 0.7 with an aqueous sodium hydroxide solution at ion exchange conditions for 0.5 to 5 hours to increase the sodium cation content to a $Na_2O/Al_2O_3$ ratio of greater than about 0.7 and to remove from about 1 to about 15 wt. % of $SiO_2$ and $Al_2O_3$ from the precursor mass;
   ii. washing said mass with water maintained at a pH within the range of 7 to 10 to remove therefrom excess sodium hydroxide; and,
   iii. at least partially dehydrating said meass at dehydrating conditions.

2. The process of claim 1 further characterized in that said hydrocarbon feed mixture contains olefins having from about 4 to about 20 carbon atoms per molecule.

3. The process of claim 1 further characterized in that said adsorption and desorption conditions include temperatures within the range of from about 25° to about 150° C. and pressures within the range of from about atmospheric to about 500 psig.

4. The process of claim 1 further characterized in that said adsorption and desorption conditions are effected in the liquid phase.

5. The process of claim 1 further characterized in that said desorbent material has an average boiling range substantially different than that of the feed mixture.

6. The process of claim 5 further characterized in that said desorbent material comprises a straight chain olefin.

* * * * *